United States Patent [19]
Haumont et al.

[11] Patent Number: 6,120,875
[45] Date of Patent: Sep. 19, 2000

[54] TRANSPARENT MICRO PERFORATED MATERIAL AND PREPARATION PROCESS

[75] Inventors: Charles Haumont, Bruxelles; Roger Legras, Lens Saint Remy, both of Belgium

[73] Assignee: Cyclopore S.A., Belgium

[21] Appl. No.: 08/430,752

[22] Filed: Apr. 27, 1995

Related U.S. Application Data

[63] Continuation of application No. 08/197,668, Feb. 16, 1994, abandoned, which is a continuation of application No. 07/707,687, May 30, 1991, abandoned.

[30] Foreign Application Priority Data

Jun. 1, 1990 [FR] France ................................. 90 06865

[51] Int. Cl.$^7$ .............................. B32B 3/24; C12M 1/12
[52] U.S. Cl. ..................... 428/131; 428/137; 428/220; 428/338; 428/333; 428/412; 428/480; 428/474.4; 428/500; 428/532; 428/918; 55/522; 210/500.21; 435/297.1; 216/87; 216/62
[58] Field of Search ..................... 428/137, 131, 428/220, 338, 333, 412, 480, 474.4, 500, 532, 918; 156/643, 644; 55/522; 210/500.21; 435/297.1; 216/87, 62

[56] References Cited

U.S. PATENT DOCUMENTS

| | | | |
|---|---|---|---|
| 3,303,085 | 2/1967 | Price et al. ............................... | 428/156 |
| 3,493,751 | 2/1970 | Davies et al. ............................ | 376/257 |
| 3,612,871 | 10/1971 | Crawford et al. ....................... | 156/643 |
| 3,677,844 | 7/1972 | Fleischer et al. ........................ | 156/644 |
| 3,713,921 | 1/1973 | Fleischer et al. ........................ | 428/131 |
| 3,852,134 | 12/1974 | Bean ........................................ | 156/643 |
| 4,778,868 | 10/1988 | Higashimura et al. ................. | 526/279 |
| 4,808,709 | 2/1989 | Onishi ..................................... | 536/112 |
| 4,830,917 | 5/1989 | Carpenter et al. .................... | 428/315.5 |
| 4,855,049 | 8/1989 | Toulemonde et al. ................ | 210/500.4 |
| 4,909,896 | 3/1990 | Ikushima et al. ....................... | 156/643 |
| 4,923,608 | 5/1990 | Flottmann et al. ................ | 210/500.25 |
| 4,956,219 | 9/1990 | Legras et al. ........................... | 343/768 |
| 5,213,721 | 5/1993 | Grendahl ................................. | 264/1.7 |

FOREIGN PATENT DOCUMENTS

| | | |
|---|---|---|
| 0 317 399 | 11/1987 | European Pat. Off. . |
| 0 325 752 | 12/1988 | European Pat. Off. . |
| 1375204 | 11/1974 | United Kingdom . |
| WO 8 705 850 | 10/1987 | WIPO . |

OTHER PUBLICATIONS

Chemical Engineering Progress, vol. 71, No. 12, Dec. 1975; pp. 55–61; M.C. Porter, "*Selecting the right Membrane*".

*Primary Examiner*—William P. Watkins, III
*Attorney, Agent, or Firm*—Blakely, Sokoloff, Taylor & Zafman

[57] ABSTRACT

The subject of the present invention is a solid material in the form of a microperforated sheet transparent to light of wavelengths in the visible and infrared, characterized in that the mean distance between two immediately neighbouring perforations is at least 5, and preferably 7 $\mu$m, and is so over each face of the material. Preferably, the mean angle of inclination of the perforations through the thickness of the material is less than 10°, even 5°. In a particular embodiment, the material is a membrane produced from a flexible polymer film with a thickness lying between 0.1 and 100 $\mu$m, more generally between 5 and 50 $\mu$m, and the perforation diameters lying between 0.01 and 15 $\mu$m. The membranes obtained according to the invention are particularly useful as support membranes for viewing in an optical microscope or in infrared spectroscopy. They may also be used as filter membranes or, amongst other applications, as a support for cell culture.

18 Claims, 3 Drawing Sheets

FIG_1

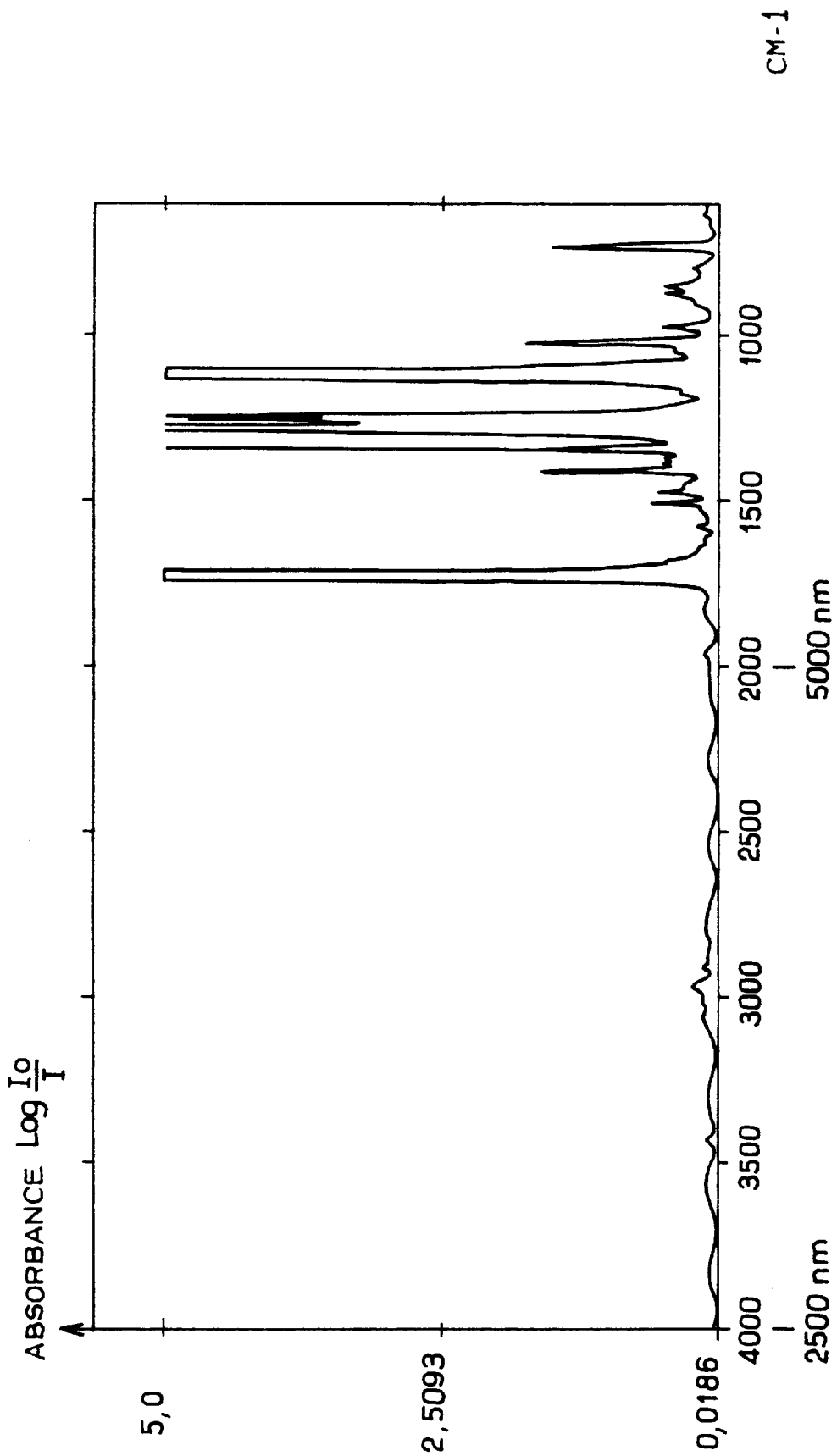
FIG._3

TRANSPARENT MICRO PERFORATED MATERIAL AND PREPARATION PROCESS

This is a continuation of application Ser. No. 08/197,668 filed Feb. 16, 1994 abandoned, which is a continuation of application Ser. No. 07/707,687 filed May 30, 1991 abandoned.

The present invention relates to a solid material in the form of a microperforated sheet transparent to visible light and to wavelengths in the infrared region.

In particular, the present invention relates to transparent membranes consisting of a microperforated transparent polymer film.

Finally, the present invention relates to a process for the preparation of the said material or the said membranes.

It is already known to obtain perforations in a solid material in sheet form by the production, in a first stage, of tracks of damage in the material by means of high-energy particles modifying the material along their trajectories and, in a second stage, by chemical treatment in order to attack the material selectively along the tracks of damage.

Several variants of the implementation of this type of process have been proposed in the state of the art. In particular, Patents U.S. Pat. No. 3,303,085, U.S. Pat. No. 3,493,751, U.S. Pat. No. 3,612,871 and Patent GB 1 375 204 may be mentioned. Other variants of the implementation of this type of process have also been envisaged in U.S. Pat. No. 3,713,921, U.S. Pat. No. 3,852,134, U.S. Pat. No. 3,677,844 and FR 2 180 215.

An improved process of this type for producing microperforation in a solid material in sheet form, together with an irradiation device for implementing this process, has been described in International Patent Application WO 87/05850.

The process described in WO 87/05850 makes it possible to produce perforated material of very high quality as regards the homogeneity of the perforations, their dimensional uniformity with, in particular, an identical diameter of the perforations on the two faces of the material.

Hitherto, however, the microperforated materials obtained by these processes have always been either opaque or at best translucent or rendered translucent by wetting.

For a long time now, microperforated materials have been sought which are transparent, and sought for many applications, for example as membranes when the material is a flexible polymer.

In the field of microbiology, and in particular that of cell culture, microporous membranes are used as a support for cell culture. Membranes are sought which are transparent in such a way as to allow the biologist to monitor cell growth by microscopy and, for example, to carry out direct staining with fluorescent dyes, the membrane not being fluorescent.

The microporous membranes for cell culture and for other applications commercially available at present are always opaque or at best translucent.

The aim of the present invention is the production of a microperforated membrane completely transparent to visible light and to wavelengths in the infrared region.

Until then, the normal practice of a person skilled in the art had been to seek membranes having the greatest possible proportion of their surface open to perforations, and hence the largest possible number of perforations per $cm^2$, in order to obtain the highest possible permeability for a given perforation diameter, the limiting factor being related only to the necessary mechanical strength of the material.

In addition, in the microperforation processes indicated above, the beam of accelerated particles was deflected in such a way as to sweep the band of material transversely in order to produce a uniform density of perforations on the material, and the angle at which the material was bombarded by the particles was made to vary up to 45° and even up to 60° in order to avoid multiple perforations, in view of the high intensity of the bombardment.

Prior to that, it was discovered fortuitously, by very greatly reducing the intensity of the particle bombardment and hence the perforation density, and at the same time by decreasing the angle of incidence at which the particle beam bombarded the material, that the material remained completely transparent to radiation in the visible and infrared regions of the spectrum while preserving a sufficient permeability of the material.

Experiments also showed that, for each perforation diameter produced, and for a given mean inclination of perforation, it was essential that a given maximum perforation density should not be exceeded if the transparency of the material was to be preserved.

These conditions in fact amount to the mean distance between two immediately neighbouring perforations always being sufficiently great on both faces of the material.

The membranes available until then had mean minimum distances between perforations of the order of 1 $\mu$m and even 0.5 $\mu$m.

According the present invention, it has been found that the mean distance between two immediately neighbouring perforations must be at least 5 $\mu$m, and preferably 7 $\mu$m, in order to obtain complete transparency to radiation in the visible and the near and middle infrared regions of the spectrum.

FIG. 3 represents the absorbance curve for a polyethylene terephthalate membrane according to the invention.

Figure 1:
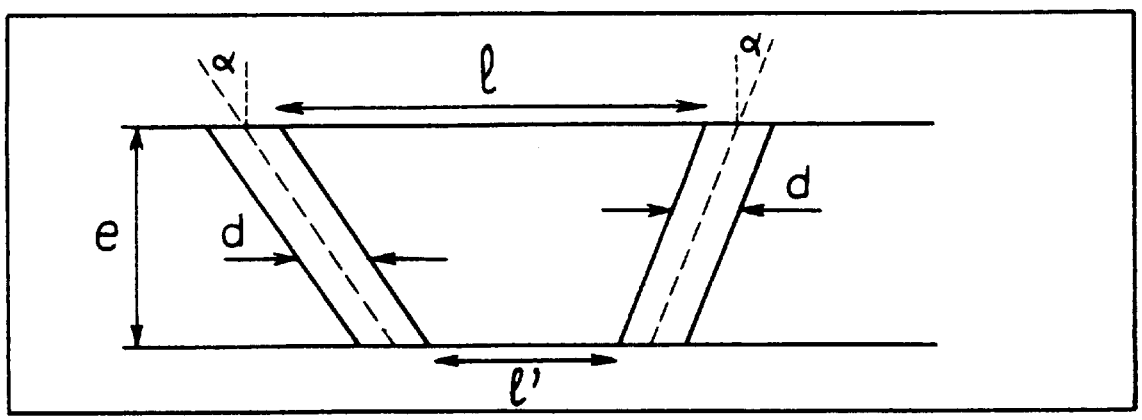
FIG. 1 represents a cross-sectional view of two neighbouring perforations.

In FIG. 1, alpha is the angle of inclination with respect to the perpendicular to the sheet of material, d is the diameter of the perforations, 1 and 1' are the respective distances between the perforations on each face of the material. In order to keep the permeability as high as possible, it is desirable for a given perforation diameter for the perforation density to be as high as possible, and hence for the distances between perforations to be as small as possible. However, if, in addition, the distances between neighbouring perforations on each face, i.e. 1 and 1', have to be greater than a given value, as has been seen, in order to maintain the transparency of the material, then the maximum possible perforation density is obtained, according to the invention, by decreasing as much as possible the angle of inclination of the perforations with respect to the perpendicular to the sheet of material.

The subject of the present invention is therefore solid materials in perforated sheet form transparent to radiation with wavelengths in the visible and infrared regions, whose main characteristic is that they consist of a material which is transparent when in the non-perforated state and in which the mean distance between two immediately neighbouring perforations on its two faces is at least 5 $\mu$m, and is preferably 7 $\mu$m.

In practice, this minimum distance between immediately neighbouring perforations will lie between 5 and 1000 $\mu$m, most often will not exceed 100 $\mu$m, or even 10 $\mu$m preferably being as small as possible, as has been seen, i.e. of the order of 7 $\mu$m, in order to obtain the highest possible permeability while preserving complete transparency.

Advantageously, according to another characteristic, the material in microperforated sheet form according to the invention is transparent to visible and infrared light when the mean inclination of the perforations through the thickness of the material does not exceed 10°, preferably 5° or even the smallest possible angle, with respect to the perpendicular to the sheet of material.

Experiments have made it possible to show that complete transparency of the material is preserved when the perforation diameter (d) and the perforation density (n=number of perforations per cm$^2$) over each face of the material, if the perforations have a mean inclination not exceeding 5°, preferably 1°, are such that, for a given mean perforation diameter d expressed in microns ($\mu$m), the perforation density n, expressed as the number of perforations per cm$^2$, does not exceed a maximum value ($n_{max}$) such that:

$$n < \left(\frac{10^4}{d+l_m}\right)^2 = n_{max}$$

where $l_m$ is the mean distance between two immediately neighbouring perforations expressed in $\mu$m, or preferably:

$$n < \left(\frac{10^4}{d+7}\right)^2 = n_{max}$$

In practice, in order to take into account the limits on the accuracy with which the perforation density is known, the density will be fixed at 90% of the maximum values given by the following formula:

$$n_{max} = \left(\frac{10^4}{d+7}\right)^2$$

When the mean angle of inclination of the perforations exceeds 5° with respect to the perpendicular to the sheet, it is of course still possible to obtain transparent microperforated materials in accordance with the present invention, but their permeability will be comparatively lower; in practice, for small perforation diameters, particularly those less than 5 $\mu$m, it is preferable not to exceed 10°.

When the mean angle of inclination exceeds 50°, the maximum perforation density not to be exceeded for a given perforation diameter also varies as a function of the thickness of the sheet of material and of the angle of inclination. The empirical relation between the perforation density and the perforation diameter may be expressed as follows:

$$n < \left(\frac{10^4}{d+l_m+2e\tan\alpha}\right)^2 = n_{max}$$

where e is the thickness of the sheet of material expressed in $\mu$m, and alpha is the mean angle of inclination of the perforations with respect to the perpendicular to the sheet; preferably $l_m$=7 $\mu$m and n=90% $n_{max}$.

In a particular embodiment, the material is a membrane produced from a flexible polymer film of thickness lying between 0.1 and 100 $\mu$m and more generally between 10 and 50 $\mu$m, the perforation diameters lying between 0.01 and 15 $\mu$m.

In practice, for perforation diameters varying between 0.01 $\mu$m and 15 $\mu$m, the maximum perforation density not to be exceeded will vary respectively between about 2×10$^6$ and 1×10$^5$ perforations/cm$^2$.

The permeability obtained, expressed as a percentage of the surface open to perforations, will, according to the invention, lie advantageously between 0.01 and 15%.

The invention is particularly advantageous as regards the small perforation diameters, for example those less than 5 $\mu$m, for which the membranes available hitherto were particularly opaque; in this case it is very advantageous to use small angles of inclination of the perforations, particularly less than 10° and preferably less than 5°, in order to obtain transparent membranes with sufficient permeability. It will also be noted that diameters below 5 $\mu$m correspond precisely to applications where the need for transparent membranes is greatest.

Synthetic material may be mentioned as a useful material according to the invention, especially transparent flexible neosynthetic polymer chosen from the polyesters, e.g. polyethylene terephthalate, the polycarbonates, e.g. bisphenol-A, the aromatic polyethers, the polysulphones and polyolefines, the polyacrylates, the polyamides, the acetates and the nitrates of cellulose.

The field of application of microporous and microperforated membranes is very extensive, but is considerably broadened as far as transparent microperforated membranes according to the invention are concerned.

Amongst others, but in a non-limiting manner, all the applications involving support membranes for viewing in an optical microscope or in infrared spectroscopy may be mentioned.

In addition, the transparent membranes obtained according to the invention may be sufficiently permeable to be used as filter membranes, for example in certain applications. Moreover, as has been seen, the materials according to the invention can be used as a support membrane for cell culture and have an even better performance for cell culture than the microporous membranes used hitherto for this type of application.

The membranes according to the invention will be able to receive a surface treatment such as a chemical treatment, for example oxidation, or a treatment with polyvinylpyrrolidone to make them hydrophilic, or a radiochemical treatment of the corona discharge or plasma type, or a photochemical treatment, for example UV or gamma radiation.

Advantageously, the support membranes for cell culture according to the invention are subjected to a suitable surface treatment favouring the adhesion, growth and differentiation of cells, or a treatment controlling the level of fixation of non-specific proteins.

Another subject of the present invention is a process in which a transparent material in non-perforated form is perforated, the process being characterised in that the mean distance between two immediately neighbouring perforations is at least 5 $\mu$m, and preferably 7 $\mu$m, on each face of the material.

As has been seen, in the process according to the invention, the inclination is preferably not greater than 10° and is preferably as small as possible, and the relation between the perforation diameter and the perforation density is as previously described.

The processes for obtaining a solid material in perforated sheet form described in the state of the art, for example in the documents cited above, are applicable to the process according to the invention inasmuch as it can be implemented by using any means of microperforation.

In a particularly suitable means of production, the material is first subjected to bombardment by high-energy particles, for example heavy ions. Each impact of the particles on the material generates a track of damage. The perforation density, related to the intensity of the bombardment, is exactly equal to the impact density. The material is then subjected to a chemical treatment in such a way as to attack the tracks of damage created by the bombardment and to obtain perforations of the desired diameter.

The bombardment by particles can be performed, for example, by means of a nuclear reactor or any other source of high-energy particles, but preferably by means of a particle accelerator. If need be, on the one hand, it will be such that the mean angle of incidence of the particle beam on the material does not exceed 5°, and is preferably 1°, with respect to the perpendicular to the sheet of material on both sides, and, on the other hand, it will be of an intensity such that the impact density (n', expressed as the number of impacts per cm²) satisfies the following equations:

$$n' < \left(\frac{10^4}{d + l_m}\right)^2 = n'_{\max}$$

where d is the mean perforation diameter expressed in $\mu$m and $l_m$ is the mean distance between two immediately neighbouring perforations, or preferably:

$$n' < \left(\frac{10^4}{d + 7}\right)^2 = n'_{\max}$$

and, once again, preferably n'=90% $n_{max}$.

If the angle of incidence exceeds 50, the relation becomes:

$$n' < \left(\frac{10^4}{d + l_m + 2e\tan\alpha}\right)^2 = n'_{\max}$$

where d, $l_m$, e and alpha have the meanings given to them previously, preferably with $l_m$=7 and n'=90% n'$_{max}$.

In order to obtain a high quality of perforation, especially as regards the homogeneity of the perforations and their dimensional uniformity, a perforation process such as that described in WO 87/05850 will preferably be used, with an irradiation device combined with an isochronous cyclotron situated upstream, eliminating in the device, if need be, the means for the inclination of the angle of incidence of the beam.

According to this technique, the impact density (or perforation density) depends, on the one hand, on the intensity of bombardment (in amperes or in numbers of particles emitted per second) and, on the other hand, on the velocity with which the sheet of material passes in front of the particle beam.

In the case in point, the material should be subjected to the smallest possible intensity of bombardment while maintaining the stability of the irradiation device and, in any case, should be very much less than that used previously. On the other hand, the velocity with which the material is moving must be increased in comparison with the previous processes.

More precisely, in order to obtain the perforation densities mentioned above, the material is subjected to bombardment by accelerated ionised heavy ions, for example argon ions, having an energy of the order of 1 to 10, more generally 5 to 6 MeV per nucleon, the beam of accelerated particles being associated with having a current lying between about 10 and 30 nanoamperes, this being produced by means of an irradiation device combined with an isochronous cyclotron situated upstream. Moreover, the sheet of material moves through the irradiation device at a velocity lying between about 30 and 50 m/minute.

The desired perforation diameter is obtained by chemical treatment such as that described in WO 87/05850. Other characteristics of this process are given in the description of WO 87/05850, to which reference should be made.

Other features and advantages of the present invention will appear in the light of the examples which follow, illustrating the invention but nevertheless without limiting its scope.

EXAMPLE 1

PREPARATION OF A TRANSPARENT MICROPERFORATED MEMBRANE

A range of microperforated membranes was fabricated from films of bisphenol-A polycarbonate or polyethylene terephthalate. The process used was that described in WO 87/05850, with adaptations to the intensity of bombardment and the velocity of movement of the polymer film, described above.

The angle of attack of the beam on the material was kept between 0° and 5°, and preferably at 1°. Complete transparency to visible light and to infrared radiation was obtained independently of the thickness of the membrane, with values less than those given in Table 1 below corresponding to a mean distance between immediately neighbouring perforations of the order of 7 $\mu$m.

In order to take into account the limits on the accuracy of the perforation density, the bombardment of the material was performed in such a way as to obtain a density equal to 90% of the maximum values listed in Table 1.

TABLE 1

MAXIMUM IMPACT DENSITY OR PERFORATION DENSITY AS A FUNCTION OF PERFORATION SIZES

| perforation diameter d ($\mu$m) | maximum perforation density (cm²) | surface open to perforations (%) |
|---|---|---|
| 0.01 to 0.1 | 2.00 10⁶ | 0.002 to 0.02 |
| 0.2 | 2.00 10⁶ | 0.06 |
| 0.4 | 1.80 10⁶ | 0.2 |
| 0.6 | 1.70 10⁶ | 0.5 |
| 0.8 | 1.60 10⁶ | 0.8 |
| 1 | 1.60 10⁶ | 1.2 |
| 2 | 1.20 10⁶ | 3.9 |
| 3 | 1.00 10⁶ | 7.1 |
| 5 | 7.00 10⁵ | 13.6 |
| 8 | 4.50 10⁵ | 22.3 |
| 10 | 3.50 10⁵ | 27.2 |
| 12 | 2.80 10⁵ | 31.3 |
| 15 | 2.50 10⁵ | 35.0 |

Appropriate values will, for example, be those given in the following Table 2:

TABLE 2

TRANSPARENT POLYETHYLENE TEREPHTHALATE OR
POLYCARBONATE MEMBRANE
(thickness 10 to 12 μm)

| perforation diameter (μm) | perforation density (no. of perf./cm$^2$) | percentage of open surface (%) |
|---|---|---|
| 0.2 | 2 10$^6$ | 0.06 |
| 0.4 | 1.6 10$^6$ | 0.2 |
| 0.6 | 1.6 10$^6$ | 0.45 |
| 0.8 | 1.6 10$^6$ | 0.8 |
| 1 | 1.6 10$^6$ | 1.26 |
| 2 | 9 10$^5$ | 2.8 |
| 3 | 4 10$^5$ | 2.83 |
| 5 | 4 10$^5$ | 7.85 |
| 8 | 1 10$^5$ | 5.03 |
| 10 | 1 10$^5$ | 7.85 |
| 12 | 1 10$^5$ | 11.31 |

For angles of attack of 10° or more on average, the process requires, to obtain complete transparency, much smaller densities and surfaces open to perforations, for example, for a material of thickness 10 μm, the values given in the following Table 3 are obtained:

TABLE 3

| pore size (μm) | PERFORATION DENSITY PER cm$^2$ Mean angle of inclination of perforations | | | |
|---|---|---|---|---|
| | 10° | 20° | 30° | 45° |
| 0.01 to 0.1 | 1.0 10$^6$ | 5.0 10$^5$ | 3.0 10$^5$ | 1.5 10$^5$ |
| 0.1 | 1.0 10$^6$ | 5.0 10$^5$ | 3.0 10$^5$ | 1.5 10$^5$ |
| 0.2 | 9.0 10$^5$ | 5.0 10$^5$ | 3.0 10$^5$ | 1.5 10$^5$ |
| 0.4 | 8.5 10$^5$ | 4.5 10$^5$ | 3.0 10$^5$ | 1.3 10$^5$ |
| 0.6 | 8.0 10$^5$ | 4.5 10$^5$ | 2.5 10$^5$ | 1.3 10$^5$ |
| 0.8 | 8.0 10$^5$ | 4.5 10$^5$ | 2.5 10$^5$ | 1.3 10$^5$ |
| 1.0 | 7.5 10$^5$ | 4.5 10$^5$ | 2.5 10$^5$ | 1.3 10$^5$ |
| 2.0 | 6.5 10$^5$ | 4.0 10$^5$ | 2.5 10$^5$ | 1.2 10$^5$ |
| 3.0 | 5.5 10$^5$ | 3.5 10$^5$ | 2.0 10$^5$ | 1.0 10$^5$ |
| 5.0 | 4.0 10$^5$ | 3.0 10$^5$ | 2.0 10$^5$ | 1.0 10$^5$ |

EXAMPLE 2

ABSORBANCE MEASUREMENTS ON VARIOUS MEMBRANES

Figure 2:
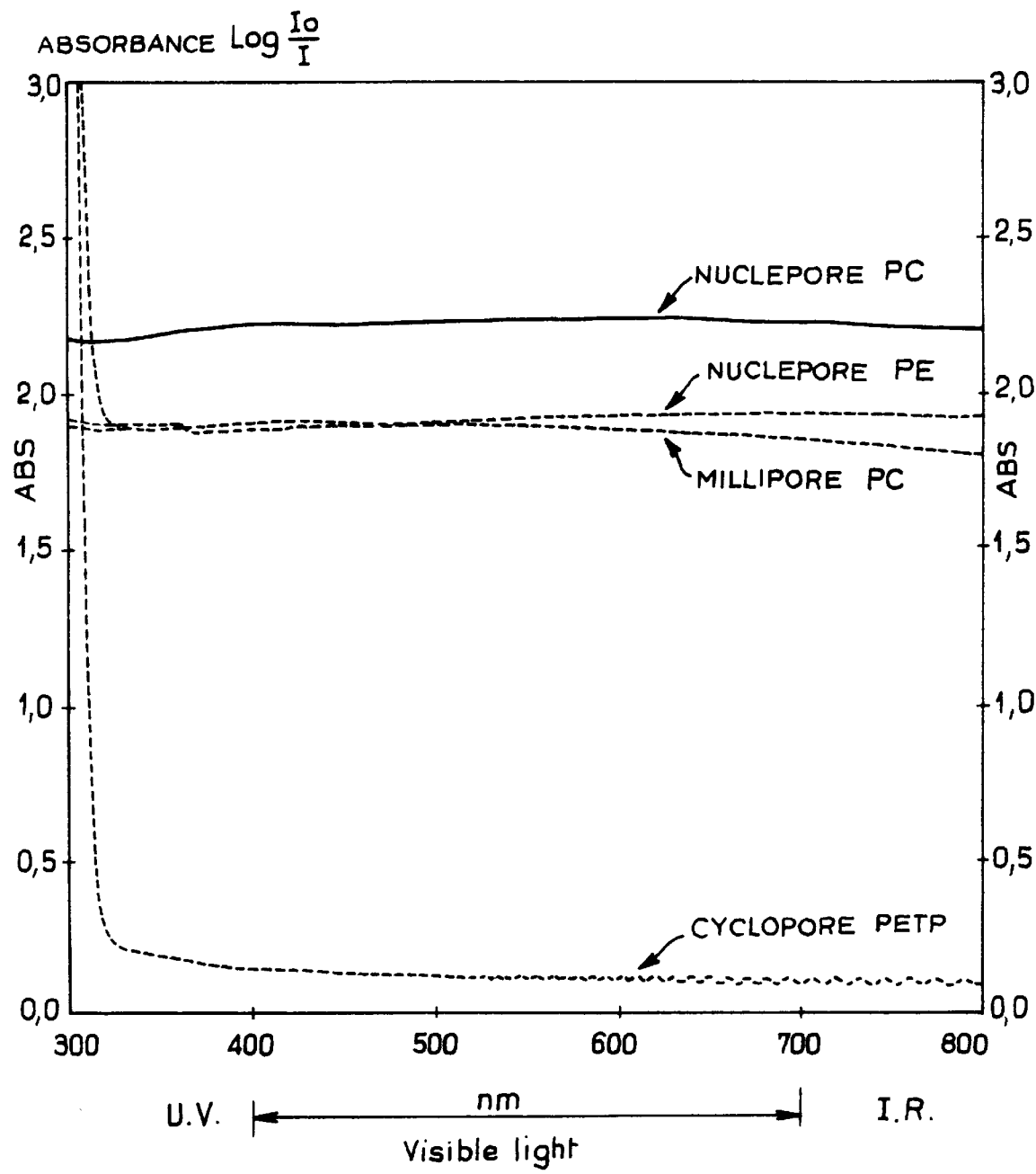
FIG. 2 represents the absorbance curves in the visible and near infrared region from 300 to 800 nm for a membrane according to the invention.

FIG. 2 represents the absorbance curves in the visible and near infrared region from 300 to 800 nm for a membrane according to the invention: "CYCLOPORE" in polyethylene terephthalate and NUCLEPORE® translucent microperforated membranes in polycarbonate (PC) or polyester (PE), and a MILLIPORE® translucent microperforated membrane.

These membranes had a thickness of about 10 μm and hole diameters of about 0.4 μm. The surface open to holes was of the order of 13% for the MILLIPORE® and NUCLEPORE® membranes and 0.2% for the CYCLOPORE membrane.

The mean distances between immediately neighbouring perforations are of the order of 0.5 to 0.9 μm and the perforation density is of the order of 1×10$^8$ cm$^{-2}$ for the NUCLEPORE® and MILLIPORE® membranes and of the order of 7 μm and 1.6×10$^6$ respectively for the CYCLOPORE membranes according to the invention.

The NUCLEPORE® and MILLIPORE® membranes have an absorbance close to the absorbance limit of the photometer, whereas the CYCLOPORE membrane shows an almost zero absorbance in the visible and infrared (FIG. 2).

FIG. 3 represents the absorbance curve for a polyethylene terephthalate membrane according to the invention of thickness 11 μm, which shows that the membrane is completely transparent in the infrared region from 2500 to 5000 nm.

The curves of FIGS. 2 and 3 show that the membranes according to the invention are transparent to wavelengths between 350 and 5000 nm.

EXAMPLE 3

TRANSPARENT MEMBRANE AS A SUPPORT IN CELL CULTURE

Cell cultures were obtained using transparent microperforated membranes according to the invention as described in Example 1. The transparent membranes had, in addition, received a chemical treatment favouring cell culture. This type of membrane was tested for its capabilities in the spreading, growth and differentiation of animal cells, especially polarised cells such as epithelial and endothelial cells.

The membranes were introduced in the form of a 25 mm diameter disc inserted into the tissue culture plates (more especially plates with standard 6 wells); the membranes had perforation sizes of 0.45 μm or 3 μm and their thickness in the two cases was 11 μm or 50 μm, while the membranes were completely transparent and non-fluorescent and made of polyethylene terephthalate.

In spite of a lower permeability with proportions of the surface open to perforations from 0.2% to 7%, the permeability was sufficient, and was even perfectly adapted to a good diffusion of the nutritive elements in the culture medium and of the products that were biosynthesised and/or transported by the cells when it was used as a support for the culture.

Thus, in order to study the differentiated cell functions, particularly for studies of epithelial cells, the membranes according to the invention, with a non-porous support made of polystyrene treated for cell culture, were compared with a microporous membrane of a MILLIPORE Millicell-CM® cell culture insert, which allowed one well of the culture plates to be divided into two compartments and made it possible to work independently on the basal and apical surfaces of the cells.

Detail of the experimental procedure:

MDCK cell culture (Madin Darby Coker Kidney cells of epithelial origin;

culture medium: MEM supplemented with 10% foetal calf serum;

membrane coating:

membrane according to the invention: none polystyrene support: none

MILLIPORE membrane for Millicell-CM®: 400 μl of type I collagen at 750 μg/ml in 45% (v/v) ethanol; and evaporation; washing with PBS.

Microscope observations by direct microscopy or phase contrast microscopy are only possible with transparent membranes according to the invention.

In addition, cell growth is greater with membranes according to the invention, as is evident from Table 4 below:

TABLE 4

| | µg of cell proteins/cm² | | |
| --- | --- | --- | --- |
| Time | Transparent membranes according to the invention | Poly-styrene | Millicell-CM ® |
| 0 h | 5 | 5 | 5 |
| 24 h | 20 | 20 | 25 |
| 48 h | 50 | 40 | 40 |
| 174 h | 125 | 45 | 60 |

What is claimed is:

1. A filtration membrane in the form of a microperforated sheet transparent to wavelengths in the visible and infrared spectrums, the sheet comprising a material transparent in the non-perforated state having perforations with a mean distance $l_m$ between circumferences of neighboring perforations between 5 µm and 100 µm on each face of the material, and having a thickness e of 0.1 to 50 µm wherein the perforations include a perforation diameter d between 0.01 and 15 µm, and a mean angle alpha of inclination through the material between 0° and 10° with respect to an axis perpendicular to the sheet of material.

2. The filtration membrane according to claim 1, wherein the mean distance $l_m$ between circumferences or neighboring perforations is between 5–10 µm.

3. The filtration membrane according to claim 1, wherein the mean angle α of inclination of the perforations is between 0° and 5° and the material has a perforation density n and a maximum perforation density $n_{max}$ such that:

$$n < n_{max} \text{ where } n_{max} = (10^4/d + l_m)^2,$$

with n=number of perforations per cm²;

d=mean perforation diameter expressed in microns; and $l_m$=mean distance between circumferences of neighboring perforations expressed in microns.

4. The filtration membrane according to claim 1, wherein the mean angle α of inclination of the perforations is between 5° and 10°, and the material has a perforation density n and a maximum perforation density $n_{max}$ such that:

$$n < n_{max} \text{ where } n_{max} = (10^4/d + l_m + 2e \tan\alpha)^2,$$

with d=mean perforation diameter expressed in microns;

$l_m$=mean distance between circumferences of neighboring perforations expressed in microns;

e=thickness of the sheet of material in microns; and

α=mean angle of inclination of the perforations with respect to the perpendicular to the sheet of material.

5. The filtration membrane according to claim 3 or 4, wherein $l_m$=7 µm and n=90% of $n_{max}$.

6. The filtration membrane according to claim 3 or 4, wherein the perforations comprise a perforation diameter d between 0.01 and 15 µm, and the material comprises a maximum perforation density $n_{max}$ between 2×10⁶ and 1×10⁵ perforations per cm².

7. A filtration membrane in the form of a microperforated sheet transparent to wavelengths in the visible and infrared spectrums, the sheet comprising a material transparent in the non-perforated state having a thickness e of 0.1 µm to 50 µm, perforations with a mean distance $l_m$ between circumferences of neighboring perforations of at least 5 µm on each face of the material and a mean angle α of inclination of the perforations through the material not greater than 10° with respect to an axis perpendicular to the sheet of material.

8. The filtration membrane according to claim 7, wherein the perforations comprise a perforation diameter between 0.01 and 5 µm.

9. The filtration membrane according to claim 7, wherein the mean distance between circumferences of neighboring perforations l m is between 5 and 10 µm.

10. The filtration membrane according to claim 7, wherein the mean angle α of inclination of the perforations is between 0° and 5°, and the material has a perforation density n and a maximum perforation density $n_{max}$ such that:

$$n < n_{max} \text{ where } n_{max} = (10^4/d + l_m)^2,$$

with n=number of perforations per cm²;

d=mean perforation diameter expressed in µm; and $l_m$=mean distance between circumferences of neighboring perforations expressed in µm.

11. The filtration membrane according to claim 7, wherein the mean angle a of inclination of the perforations is between 5° and 10°, and the material comprises a perforation density n and a maximum perforation density $n_{max}$ such that:

$$n < n_{max} \text{ where } n_{max} = (10^4/d + l_m + 2e \tan\alpha)^2,$$

with d=mean perforation diameter expressed in µm;

$l_m$=mean distance between circumferences of two immediately neighboring perforations expressed in µm;

e=thickness of the sheet of material in µm; and

α=mean angle of inclination of the perforations with respect to the perpendicular to the sheet of material.

12. The filtration membrane according to claim 10 or 11, wherein $l_m$=7 µm and n=90% of $n_{max}$.

13. The filtration membrane according to claim 10 or 11, wherein the perforations comprise a perforation diameter d between 0.01 and 15 µm, and the material comprises a maximum perforation density $n_{max}$ between 2×10⁶ and 1×10⁵ perforations per cm².

14. The filtration membrane according to claim 1, wherein the material comprises a synthetic material selected from the group consisting of polyesters, polycarbonates, aromatic polyethers, polysulphones, polyolefines, polyacrylates, polyamides, acetates and nitrates of cellulose.

15. The filtration membrane according to claim 1, wherein the material comprises a synthetic material selected from the group consisting of polyethylene terephthalate and bisphenol-A polycarbonate.

16. The filtration membrane according to claim 1, wherein the material comprises a flexible polymer having a thickness e between 10 and 50 µm.

17. A filtration membrane according to claim 1 having a perforation density n between 1×10⁵ and 2×10⁶ perforations per cm².

18. The filtration membrane according to claim 1, wherein the filtration membrane comprises a cell culture support membrane.

* * * * *